(12) United States Patent
Ling et al.

(10) Patent No.: US 11,981,616 B2
(45) Date of Patent: May 14, 2024

(54) METHOD FOR PREPARING 3,3'-DIAMINOBENZIDINE

(71) Applicants: HUBEI HUIDA HIGH-TECH CO., LTD., Hubei (CN); BORUN HIGH-TECH CO., LTD., Beijing (CN)

(72) Inventors: Yun Ling, Beijing (CN); Yongfang Li, Beijing (CN); Kun Wang, Beijing (CN); Lizhu Chen, Beijing (CN); Wei Yin, Beijing (CN); Jinying Zhang, Beijing (CN)

(73) Assignees: Hubei Huida High-Tech Co., Ltd, Jingzhou (CN); Borun High-Tech Co., Ltd., Beijing (CN)

( * ) Notice: Subject to any disclaimer, the term of this patent is extended or adjusted under 35 U.S.C. 154(b) by 0 days.

(21) Appl. No.: 18/552,016

(22) PCT Filed: Jan. 12, 2022

(86) PCT No.: PCT/CN2022/071586
§ 371 (c)(1),
(2) Date: Sep. 22, 2023

(87) PCT Pub. No.: WO2022/199226
PCT Pub. Date: Sep. 29, 2022

(65) Prior Publication Data
US 2024/0109835 A1    Apr. 4, 2024

(30) Foreign Application Priority Data

Mar. 23, 2021 (CN) .......................... 202110308372.0

(51) Int. Cl.
C07C 209/68 (2006.01)
C07C 209/22 (2006.01)
C07C 209/84 (2006.01)

(52) U.S. Cl.
CPC .......... *C07C 209/22* (2013.01); *C07C 209/84* (2013.01)

(58) Field of Classification Search
CPC ............................ C07C 211/55; C07C 211/56
See application file for complete search history.

(56) References Cited

U.S. PATENT DOCUMENTS

| | | | | |
|---|---|---|---|---|
| 3,865,876 A | * | 2/1975 | Chenevey | C07C 209/10 564/407 |
| 3,943,175 A | * | 3/1976 | Druin | C07C 211/54 564/309 |
| 4,433,168 A | * | 2/1984 | Schubert | C07C 209/84 564/309 |
| 5,041,666 A | * | 8/1991 | Ward | C07C 211/50 564/309 |
| 5,235,105 A | * | 8/1993 | Vorwerk | C07C 209/84 564/309 |
| 6,835,854 B1 | * | 12/2004 | Maner | C07C 209/36 564/309 |
| 6,979,749 B2 | * | 12/2005 | Bavikar | C07C 231/12 564/309 |

FOREIGN PATENT DOCUMENTS

| | | |
|---|---|---|
| CN | 1580038 A | 2/2005 |
| CN | 102030726 A | 4/2011 |
| CN | 102070465 A | 5/2011 |
| CN | 102173994 A | 9/2011 |
| CN | 108191674 A | 6/2018 |
| CN | 108218711 A | 6/2018 |
| CN | 112920054 A * | 6/2021 |
| CN | 112920054 A | 6/2021 |

(Continued)

OTHER PUBLICATIONS

International Search Report and Written Opinion for International Application PCT/CN2022/071586 (ISA/CN) dated Apr. 1, 2022 w/English translation (12 pages).
1st Office Action for Priority Application No. CN2021103083720 dated Jan. 19, 2023 w/Search Report (6 pages).
Notice of Allowance for Priority Application No. CN2021103083720 dated Apr. 20, 2023 (1 page).
Yang, Zhongmin, "Synthesis of 4,4'-Bis(trifluoromethyl)-2,2'-diaminobiphenyl" Inner Mongolia Petrochemical Industry, No. 11, Dec. 31, 2015 pp. 24-26.

(Continued)

*Primary Examiner* — Alexander R Pagano
(74) *Attorney, Agent, or Firm* — Alston & Bird LLP

(57) ABSTRACT

A method for preparing 3,3'-diaminobenzidine, the method comprising the following steps: subjecting 4,4'-biphenol and N,N-dimethylsulfamoyl chloride to an esterification reaction in a specified solvent at 40-70° C. to obtain 4,4'-biphenyl bis(N,N-dimethylaminosulfonate) as a first intermediate; subjecting the 4,4'-biphenyl bis(N,N-dimethylaminosulfonate) to a chlorination reaction with a chlorinating reagent under acidic conditions to obtain 3,3'-dichloro-4,4'-biphenyl bis(N,N-dimethylaminosulfonate) as a second intermediate; subjecting the second intermediate 3,3'-dichloro-4,4'-biphenyl bis(N,N-dimethylaminosulfonate) to an ammonolysis reaction with anammoniation reagent in the presence of a combined catalyst to obtain a crude product of 3,3',4,4'-tetraaminobiphenyl, wherein the combined catalyst is a mixture of proline, a cuprous salt and a phase transfer catalyst; and subjecting the crude product of 3,3',4,4'-tetraaminobiphenyl to a post-treatment to obtain a purified 3,3',4,4'-tetraaminobiphenyl product. In the present invention, 4,4'-biphenol is used as a raw material, a brand-new synthesis route is used, the product purity is high, and pollution of three kinds of waste is reduced.

10 Claims, 1 Drawing Sheet

(56) References Cited

FOREIGN PATENT DOCUMENTS

| | | | |
|---|---|---|---|
| JP | 49011213 B | * | 3/1974 |
| JP | 2010083809 A | * | 4/2010 |
| JP | 2010083809 A | | 4/2010 |
| JP | 2010083909 A | * | 4/2010 |
| JP | 2010083909 A | | 4/2010 |
| JP | 2015013830 A | | 1/2015 |
| TW | 623512 B | | 5/2018 |
| WO | WO-2022199226 A1 | * | 9/2022 |

OTHER PUBLICATIONS

Cui, Yumin et al., "*Synthesis of 3,3'-Dichloro-4,4-diaminophenyl benzene,*" Chemistry No. 11, Dec. 31, 2011, pp. 715-717 and 726.
Ruan, Jingbo et al., "*Synthesis of 2,2',5,5'-tetraaminobiphenyl*" Chemical Enterprise Management, May 31, 2020 pp. 176-177.
Written Opinion of the International Searching Authority for PCT/CN2022/071586 (ISA/CN) dated Apr. 1, 2022 (5 pages, English translation).

\* cited by examiner

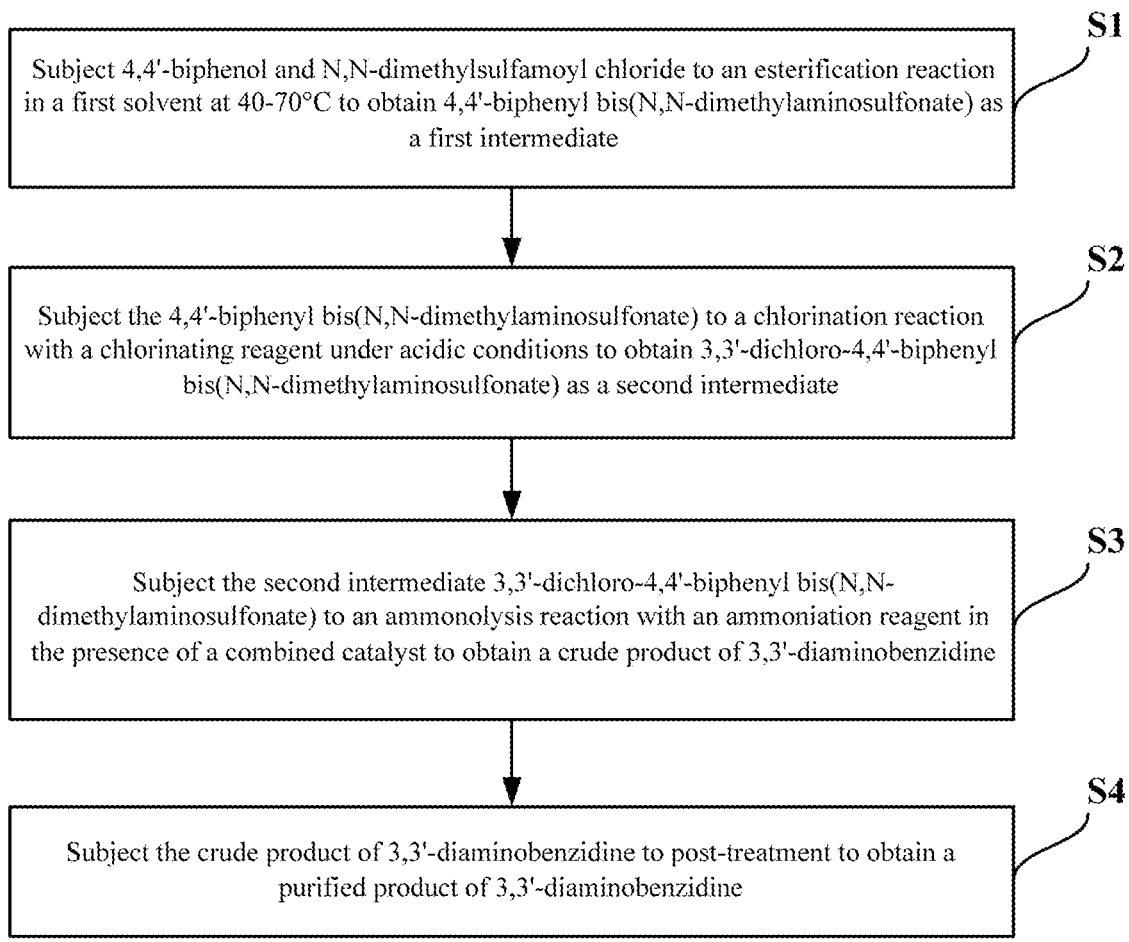

METHOD FOR PREPARING 3,3'-DIAMINOBENZIDINE

CROSS-REFERENCE TO RELATED APPLICATIONS

The present application is a national phase entry of International Application No. PCT/CN2022/071586, filed Jan. 12, 2022, which claims priority to Chinese Application No. 202110308372.0, filed Mar. 23, 2021, each of which is incorporated herein by reference in its entirety.

FIELD OF THE INVENTION

The present invention belongs to the technical field of synthesis of compounds, and specifically relates to a method for preparing 3,3'-diaminobenzidine.

BACKGROUND OF THE INVENTION 3,3'-Diaminobenzidine (DAB) is a high-grade polymer material monomer, which is mainly used for synthesis of heat-resistant polymer resins and synthetic fibers. Polymer products synthesized with the DAB as a monomer have ultra-high heat resistance, flame retardant property, dimensional thermal stability, chemical resistance at high temperature, wearing comfort and other properties, which are incomparable and irreplaceable to other materials. With continuous development of the global economy and continuous improvement of the scientific and technological level in the world, demands for aviation, aerospace, military industry, machinery, construction and other aspects will be expanded continuously. Therefore, research and development of DAB products have attracted widespread attention from relevant industries at home and abroad, and deep innovation of synthesis methods of 3,3'-diaminobenzidine has profound practical significance.

In the prior art, methods for preparing DAB mainly include the following synthesis routes.

(1) Starting from o-nitroaniline being a monobenzene ring raw material, which is subjected to iodization, amino protection, bimolecular coupling, deprotection, hydrogenation reduction and other steps to prepare a DAB target product. However, the synthesis route has many steps, a low total yield and a large amount of three kinds of wastes produced, thus being not suitable for further expansion to industrial-scale production.

(2) Starting from biphenyl raw materials, the routes may be specifically divided into two routes, one of which starts from 4,4'-biphenyldiamine and the other of which starts from dichlorobiphenyldiamine. According to the synthesis route using 4,4'-biphenyldiamine, the approaches of amino protection, nitrification, deprotection and hydrogenation reduction are required to obtain a target product, and the synthesis route has the shortcomings of a long route, a low yield, low process safety, a large amount of three kinds of wastes and the like. The synthesis route using dichlorobiphenyldiamine has a short route and has been widely used at present. However, the synthesis route has the defects of many side reactions, making it difficult to guarantee the product purity and the like. Meanwhile, according to the synthesis method, a large number of heavy metal salts are required to be used as a catalyst, leading to high difficulty in the treatment of three kinds of wastes, so that further optimization and improvement need to be conducted on the synthesis method.

At present, improvement solutions for optimizing the synthesis route using dichlorobiphenyldiamine have been reported, which can effectively reduce the difficulty in the treatment of three kinds of wastes. However, the problems have still been not solved yet that the route has many side reactions and the product quality is affected.

BRIEF DESCRIPTION OF THE INVENTION

In view of the above problems, the present invention provides a method for preparing 3,3'-diaminobenzidine to overcome the above problems or at least partially solve the above problems.

A purpose of the present invention is to provide a safe, green and efficient method for preparing 3,3'-diaminobenzidine in which 4,4'-biphenol is used as a raw material, a brand-new synthesis route is used, the product purity is high, and pollution of three kinds of wastes is reduced.

A further purpose of the present invention is to promote efficient conversion of 4,4'-biphenyl bis(N,N-dimethylaminosulfonate) as a first intermediate to a second intermediate by optimizing parameters of a chlorination reaction, thereby increasing the overall reaction yield.

In particular, according to one aspect of an embodiment of the present invention, a method for preparing 3,3'-diaminobenzidine is provided. The method includes:

step S1: subjecting 4,4'-biphenol and N,N-dimethylsulfamoyl chloride to an esterification reaction in a first solvent at 40-70° C. to obtain 4,4'-biphenyl bis(N,N-dimethylaminosulfonate) as a first intermediate;

step S2: subjecting the 4,4'-biphenyl bis(N,N-dimethylaminosulfonate) to a chlorination reaction with a chlorinating reagent under acidic conditions to obtain 3,3'-dichloro-4,4'-biphenyl bis(N,N-dimethylaminosulfonate) as a second intermediate;

step S3: subjecting the second intermediate 3,3'-dichloro-4,4'-biphenyl bis(N,N-dimethylaminosulfonate) to an ammonolysis reaction with an ammoniation reagent in the presence of a combined catalyst to obtain a crude product of 3,3'-diaminobenzidine, where a mixture of proline, a cuprous salt and a phase transfer catalyst is used as a first catalyst; and step S4: subjecting the crude product of 3,3'-diaminobenzidine to post-treatment to obtain a purified product of 3,3'-diaminobenzidine.

Optionally, in step S1, the molar amount of the N,N-dimethylsulfamoyl chloride is 2.2-3 times of that of the 4,4'-biphenol;

and the first solvent is one of or a mixture of more of tetrahydrofuran, dioxane, N,N-dimethylformamide, sulfolan and toluene, and the volume amount of the first solvent is 4-10 times of the mass of the 4,4'-biphenol.

Optionally, in step S2, the chlorinating reagent includes concentrated hydrochloric acid and sodium chlorate;

the volume amount of the concentrated hydrochloric acid is 1-4 times of the mass of the 4,4'-biphenol;

and the molar amount of the sodium chlorate is 25-50% of that of the 4,4'-biphenol.

Optionally, the volume amount of the concentrated hydrochloric acid is 2-3 times of the mass of the 4,4'-biphenol;

and the molar amount of the sodium chlorate is 35-40% of that of the 4,4'-biphenol.

Optionally, in step S2, the chlorination reaction is carried out at a temperature of 50-90° C. for 5-10 h.

Optionally, the chlorination reaction is carried out at a temperature of 75-85° C.

Optionally, in step S3, the ammoniation reagent includes one or more of liquid ammonia, ammonia water and an ammonia-methanol solution;

and the ammonolysis reaction is carried out at a temperature of 170-180° C. and a pressure of 2.5-3.5 Mpa for 5-10 h.

Optionally, in step S3, the mass amount of the proline is 1.0-5.0% of the mass of the 3,3'-dichloro-4,4'-biphenyl bis(N,N-dimethylaminosulfonate);

the cuprous salt includes one or more of cuprous chloride, cuprous sulfate and cuprous nitrate, and the mass amount of the cuprous salt is 0.1-0.5% of the mass of the 3,3'-dichloro-4,4'-biphenyl bis(N,N-dimethylaminosulfonate);

and the phase transfer catalyst includes one or more of tetrabutylammonium bromide, tetrabutylammonium chloride, triethylbenzylammonium bromide, triethylbenzylammonium chloride and an imidazoline quatemary ammonium salt, and the mass amount of the phase transfer catalyst is 1.0-5.0% of the mass of the 3,3'-dichloro-4,4'-biphenyl bis(N,N-dimethylaminosulfonate).

Optionally, the step S4 specifically includes:

cooling the crude product of 3,3'-diaminobenzidine to 10-15° C. under a protective atmosphere;

washing the crude product of 3,3'-diaminobenzidine;

dissolving the washed crude product of 3,3'-diaminobenzidine in a second solvent, and adding a decolorizing agent for decolorization treatment;

conducting filtration, and cooling a resulting filtrate to 10-15° C. for crystallization; and conducting filtration and drying to obtain the purified product of 3,3'-diaminobenzidine.

Optionally, the step S1 and the step S2 are performed in a same reactor.

According to the method for preparing 3,3'-diaminobenzidine provided by an embodiment of the present invention, a brand-new synthesis route is used, and the target product is prepared by the approach of subjecting the 4,4'-biphenol as a basic raw material to esterification with the N,N-dimethylsulfamoyl chloride, followed by selective chlorination and finally ammonolysis (amino substitution) with the special combined catalyst. The method has innovative significance. By means of the method of the present invention, safe, green and efficient production of the 3,3'-diaminobenzidine can be realized, and pollution of "three kinds of wastes" is reduced. Meanwhile, the method of the present invention also has the advantages of smooth process, mild reaction conditions, cheap and readily available raw materials, high product purity, easy industrialization and the like.

Further, in the method for preparing 3,3'-diaminobenzidine provided by an embodiment of the present invention, a highly selective process of the chlorination reaction can be promoted by screening and optimizing various reaction parameters of the chlorination reaction. Specifically, due to a directing effect of a sulfonamide ester group, an adjacent site 3,3' becomes a chlorination site. Then, by adjusting the composition and temperature of the chlorinating reagent, the reaction activity is moderate, and a passivation effect of a chlorine substituent is achieved, so as to avoid a further polychlorination reaction. Accordingly, efficient conversion of the first intermediate 4,4'-biphenyl bis(N,N-dimethylaminosulfonate) to the second intermediate 3,3'-dichloro-4,4'-biphenyl bis(N,N-dimethylaminosulfonate) is promoted, thereby increasing the overall reaction yield.

Further, in the method for preparing 3,3'-diaminobenzidine provided by an embodiment of the present invention, the esterification reaction and the chlorination reaction may be carried out by a "one-pot method", that is to say, the step S1 and the step S2 are performed in a same reactor, so that the intermediate products need not to be separated, and the operation process is simplified.

According to detailed descriptions of specific embodiments of the present invention in combination with the attached drawings below, the above and other purposes, advantages and features of the present invention will be better understood by persons skilled in the art.

BRIEF DESCRIPTION OF THE DRAWINGS

Some specific embodiments of the present invention are described in detail in an exemplary rather than restrictive manner by reference to the attached drawings. Same numerals in the attached drawings represent same or similar parts or components. Persons skilled in the art shall understand that these drawings are not necessarily drawn in a scale. In the attached drawings:

FIG. 1 is a schematic flow diagram of a method for preparing 3,3'-diaminobenzidine according to an embodiment of the present invention.

DETAILED DESCRIPTION

Technical solutions of the present invention are further explained in combination with specific embodiments below. However, it should be understood that the present invention is not limited to the specific embodiments.

In an embodiment of the present invention, a method for preparing 3,3'-diaminobenzidine is provided, where a reaction equation of the preparation route is shown as follows:

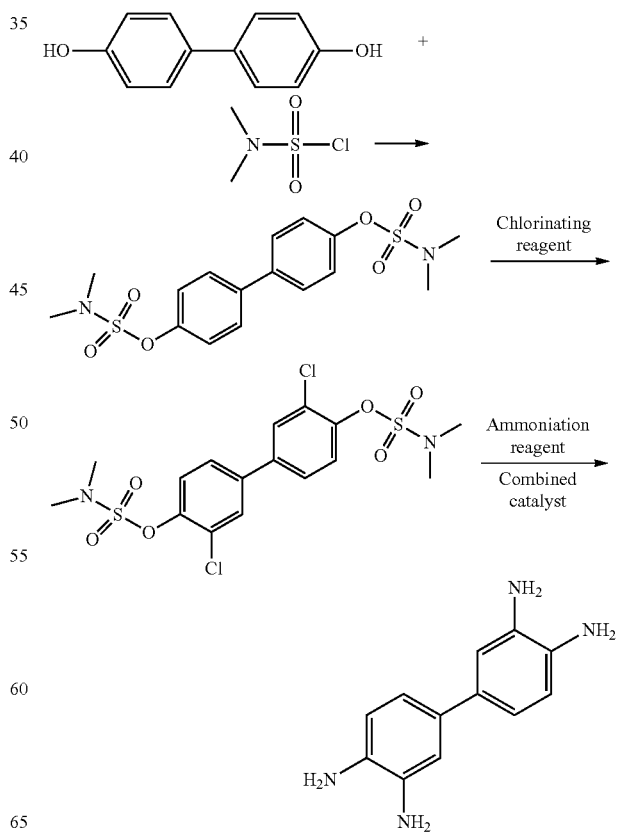

Specifically, the method for preparing 3,3'-diaminobenzidine includes the following steps:

- step S1: subjecting 4,4'-biphenol and N,N-dimethylsulfamoyl chloride to an esterification reaction in a first solvent at 40-70° C. to obtain 4,4'-biphenyl bis(N,N-dimethylaminosulfonate) as a first intermediate;
- step S2: subjecting the 4,4'-biphenyl bis(N,N-dimethylaminosulfonate) to a chlorination reaction with a chlorinating reagent under acidic conditions to obtain 3,3'-dichloro-4,4'-biphenyl bis(N,N-dimethylaminosulfonate) as a second intermediate;
- step S3: subjecting the second intermediate 3,3'-dichloro-4,4'-biphenyl bis(N,N-dimethylaminosulfonate) to an ammonolysis reaction with an ammoniation reagent in the presence of a combined catalyst to obtain a crude product of 3,3'-diaminobenzidine, where a mixture of proline, a cuprous salt and a phase transfer catalyst is used as a first catalyst; and
- step S4: subjecting the crude product of 3,3'-diaminobenzidine to post-treatment to obtain a purified product of 3,3'-diaminobenzidine.

According to the method for preparing 3,3'-diaminobenzidine provided by an embodiment of the present invention, a brand-new synthesis route is used, the target product is prepared by the approach of subjecting the 4,4'-biphenol as a basic raw material to sulfonyl esterification, followed by chlorination and ammonolysis. The method has innovative significance. By means of the method of the present invention, safe, green and efficient production of the 3,3'-diaminobenzidine can be realized, and pollution of "three kinds of wastes" is reduced. Meanwhile, the method of the present invention also has the advantages of smooth process, mild reaction conditions, cheap and readily available raw materials, high product purity, easy industrialization and the like.

In an embodiment of the present invention, the step S1 may specifically include: putting 4,4'-biphenol as a raw material and the first solvent to a reactor in sequence, and conducting stirring for uniform mixing; slowly adding N,N-dimethylsulfamoyl chloride in a flowing sate under a normal temperature condition; after the addition is completed, controlling the temperature in the reactor to 40-70° C. to carry out a reaction continuously for 1-3 h; tracking the reaction by HPLC until the reaction is completed; and then transferring a reaction solution (containing 4,4'-biphenyl bis(N,N-dimethylaminosulfonate) as the first intermediate) to an autoclave for being directly used in a next reaction. Certainly, in some other embodiments, after the reaction is completed, the reaction solution may also be left in the reactor for a next reaction.

In step S1, the molar amount of the N,N-dimethylsulfamoyl chloride is 2.2-3 times, preferably 2.3-2.5 times, of that of the 4,4'-biphenol. The first solvent may be one of or a mixture of more of tetrahydrofuran, dioxane, N,N-dimethylformamide, sulfolan, toluene and the like. The volume amount of the first solvent is 4-10 times, preferably 5-7 times, of the mass of the 4,4'-biphenol. Preferably, in step S1, the esterification reaction is carried out at a temperature of 50-60° C. The process of the esterification reaction of the 4,4'-biphenol is promoted by optimizing various parameters of the esterification reaction.

In step S2, the chlorinating reagent is a reagent capable of producing chlorine gas ($Cl_2$). In an embodiment of the present invention, the chlorinating reagent in step S2 may include concentrated hydrochloric acid and sodium chlorate. The concentrated hydrochloric acid is used as both an acidifying agent and a substrate for producing chlorine gas by reacting with the sodium chlorate. In order to promote smooth progress of the chlorination reaction, the volume amount of the concentrated hydrochloric acid may be 1-4 times of the mass of the 4,4'-biphenol, preferably 2-3 times of the mass of the 4,4'-biphenol. The molar amount of the sodium chlorate may be 25-50% of that of the 4,4'-biphenol, preferably 35-40% of that of the 4,4'-biphenol.

Correspondingly, in step S2, the chlorination reaction may be carried out at a temperature of 50-90° C. for 5-10 h. Preferably, the chlorination reaction may be carried out at a temperature of 75-85° C.

In an embodiment of the present invention, the step S2 may specifically include: stirring and mixing the reaction solution obtained in step S1 and concentrated hydrochloric acid uniformly in a reactor; slowly adding an aqueous solution of sodium chlorate in a flowing state under a normal temperature condition; after the addition is completed, raising the temperature to 50-90° C., and conducting stirring continuously to carry out a reaction for 5-10 h; tracking the reaction by HPLC until the conversion of the first intermediate 4,4'-biphenyl bis(N,N-dimethylaminosulfonate) is completed; cooling the reaction system to normal temperature, and transferring the reaction system to a washing kettle; and adding water, conducting filtration, and then washing a filter cake with water for two times and methanol for one time, followed by filtration and drying to obtain a crude product of 3,3'-dichloro-4,4'-biphenyl bis(N,N-dimethylaminosulfonate) as a second intermediate.

In the method for preparing 3,3'-diaminobenzidine provided by an embodiment of the present invention, a highly selective process of the chlorination reaction can be promoted by screening and optimizing various reaction parameters of the chlorination reaction. Specifically, due to a directing effect of a sulfonamide ester group, an adjacent site 3,3' of the sulfonamide ester group becomes a chlorination site. Then, by adjusting the composition and temperature of the chlorinating reagent, the reaction activity is moderate, and a passivation effect of a chlorine substituent is achieved, so as to avoid a further polychlorination reaction. Accordingly, efficient conversion of the first intermediate 4,4'-biphenyl bis(N,N-dimethylaminosulfonate) to the second intermediate 3,3'-dichloro-4,4'-biphenyl bis(N,N-dimethylaminosulfonate) is promoted, thereby increasing the overall reaction yield.

In some embodiments, the step S1 and the step S2 may be performed in different reactors. In some other embodiments, the step S1 and the step S2 may be performed in a same reactor, and that is to say, the esterification reaction and the chlorination reaction may be carried out by a "one-pot method". In this way, the intermediate products need not to be separated, and the operation process is simplified.

In step S3, the ammoniation reagent is a reagent capable of releasing NH3, such as one of or a mixture of more of liquid ammonia, ammonia water, an ammonia-methanol solution and the like, and is preferably ammonia water to reduce the cost of raw materials. The amount of the ammoniation reagent is appropriate to ensure that chloro and a sulfonamide ester group in the 3,3'-dichloro-4,4'-biphenyl bis(N,N-dimethylaminosulfonate) can be completely substituted with amino. Although the NH3 released by the ammoniation reagent is theoretically used with the 3,3'-dichloro-4,4'-biphenyl bis(N,N-dimethylaminosulfonate) at a molar ratio of 4:1, considering possible loss in reaction operation and the influence of actual operating conditions, in practical applications, the molar ratio of NH3 to the 3,3'-dichloro-4,4'-biphenyl bis(N,N-dimethylaminosulfonate) may be greater than 4:1.

In step S3, the proline may be subjected to complexation with the cuprous salt to achieve a catalytic effect on an amino substitution reaction. In order to ensure the catalytic effect on the amino substitution reaction, based on the intermediate 3,3'-dichloro-4,4'-biphenyl bis(N,N-dimethylaminosulfonate), the mass amount of the proline may be 1.0-5.0% of the mass of the 3,3'-dichloro-4,4'-biphenyl bis(N,N-dimethylaminosulfonate).

The cuprous salt may be a cuprous salt commonly used, such as one or more of cuprous chloride, cuprous sulfate, cuprous nitrate and the like. In order to ensure the catalytic effect on the amino substitution reaction, based on the intermediate 3,3'-dichloro-4,4'-biphenyl bis(N,N-dimethylaminosulfonate), the mass amount of the cuprous salt may be 0.1-0.5% of the mass of the 3,3'-dichloro-4,4'-biphenyl bis(N,N-dimethylaminosulfonate). Preferably, the mass amount of the cuprous salt may be 0.15-0.25% of the mass of the 3,3'-dichloro-4,4'-biphenyl bis(N,N-dimethylaminosulfonate).

The phase transfer catalyst may include one or more of tetrabutylammonium bromide, tetrabutylammonium chloride, triethylbenzylammonium bromide, triethylbenzylammonium chloride, tetrapropylammonium bromide, an imidazoline quaternary ammonium salt and the like. In order to ensure the catalytic effect on the amino substitution reaction, based on the intermediate 3,3'-dichloro-4,4'-biphenyl bis(N,N-dimethylaminosulfonate), the mass amount of the phase transfer catalyst may be 1.0-5.0% of the mass of the 3,3'-dichloro-4,4'-biphenyl bis(N,N-dimethylaminosulfonate). Preferably, the mass amount of the phase transfer catalyst is 2.0-2.5% of the mass of the 3,3'-dichloro-4,4'-biphenyl bis(N,N-dimethylaminosulfonate).

By using the proline and a small amount of the cuprous salt and the phase transfer catalyst to form a combined catalyst, the amount of the cuprous salt can be greatly reduced under the premise of efficiently promoting the smooth progress of the amino substitution reaction, so that the pressure of post-treatment of high-concentration heavy metal salt wastewater is effectively reduced, pollution of "three kinds of wastes" is reduced, the method is more friendly to the ecological environment, and the wastewater treatment cost is reduced.

Further, by using the novel combined catalyst formed by the proline and the phase transfer catalyst with assistance of the cuprous salt, the ammonolysis reaction (amino substitution reaction) can be carried out under milder conditions, and it can also be ensured that the reaction is carried out smoothly and completely. Preferably, in step S3, the ammonolysis reaction may be carried out at a temperature of 170-180° C. and a pressure of 2.5-3.5 Mpa for 5-10 h.

In an embodiment of the present invention, the step S3 may specifically include: putting a crude product of the second intermediate 3,3'-dichloro-4,4'-biphenyl bis(N,N-dimethylaminosulfonate) and ammonia water to a beater in sequence, conducting beating, and lowering the temperature to be less than 10° C.; transferring a resulting mixture to an autoclave in which a combination of proline, cuprous chloride and tetrabutylammonium chloride as a phase transfer catalyst is added in advance, maintaining the system temperature to be lower than 10° C., conducting nitrogen replacement for 3-4 times, and supplementing the ammonia water to a calculated amount; and sealing the autoclave, conducting stirring, raising the temperature to 170-180° C., and carrying out a reaction while maintaining the temperature at a pressure of 2.5-3.5 MPa for 5-10 h.

By using the novel combined catalyst, the ammonolysis reaction in the preparation method of the present invention is carried out under milder conditions including reaction temperature and reaction pressure, so that not only is energy consumption reduced, but also the safety of a process flow is improved. The method is more suitable for industrial production.

In an embodiment of the present invention, the step S4 may include the steps of washing, decolorization and crystallization of the crude product of 3,3'-diaminobenzidine. Specifically, the crude product of 3,3'-diaminobenzidine obtained in step S3 is cooled to 10-15° C. under a protective atmosphere (such as nitrogen atmosphere) first. Then, the crude product of 3,3'-diaminobenzidine is washed with ammonia water and water in sequence. The washed crude product of 3,3'-diaminobenzidine is dissolved in a second solvent, and a decolorizing agent is added for decolorization treatment. Then, filtration is conducted, and a resulting filtrate is cooled to 10-15° C. for crystallization and precipitation of the 3,3'-diaminobenzidine. Finally, filtration and drying are conducted to obtain the purified product of 3,3'-diaminobenzidine.

More specifically, in step S4, the reaction system obtained in step S3 (containing the crude product of 3,3'-diaminobenzidine) is cooled to 70-80° C., discharged to a cooling kettle, continuously cooled to 10-15° C., transferred to a washing kettle, and then washed with ammonia water (for example, the concentration of the ammonia water may be 25 wt %) for many times (such as. 3 times) and washed with water for many times (such as 3 times). The whole process is performed under the protection of nitrogen to prevent discoloration and other phenomena of the 3,3'-diaminobenzidine in the air. Then, the washed crude product is transferred to a decolorizing kettle, the second solvent and the decolorizing agent are added, and heating reflux is conducted for decolorization for about 1 h under the protection of nitrogen replacement. After the decolorization is completed, filtration is conducted at high temperature, and a resulting filtrate is cooled to 10-15° C. for crystallization and precipitation of the 3,3'-diaminobenzidine. Finally, suction filtration is conducted, and a filter cake is subjected to vacuum drying to obtain a finished product of 3,3'-diaminobenzidine.

In the step of decolorization, the second solvent may be water, methanol, ethanol or other solvents capable of dissolving the 3,3'-diaminobenzidine, and is preferably methanol. When the methanol is used, preferably, the mass amount of the methanol may be 20-35 times of that of the crude product of 3,3'-diaminobenzidine. More preferably, the mass amount of the methanol may be 25-30 times of that of the crude product of 3,3'-diaminobenzidine. By selecting an appropriate solvent and an amount thereof, it is ensured that the crude product of 3,3'-diaminobenzidine can be completely dissolved, and the effects of decolorization and a subsequent crystallization are ensured.

In the step of decolorization, the decolorizing agent may be activated carbon, active clay or other adsorptive decolorizing agents, and is preferably activated carbon. When the activated carbon is used, preferably, the amount of the activated carbon may be 2-15 wt % of that of the crude product of 3,3'-diaminobenzidine. More preferably, the amount of the activated carbon may be 5-10 wt % of that of the crude product of 3,3'-diaminobenzidine. By selecting an appropriate decolorizing agent and an amount thereof, a decolorization effect of the crude product of 3,3'-diaminobenzidine is ensured, and the purity of the 3,3'-diaminobenzidine product is further improved.

After the above reactions are completed, the crude product of 3,3'-diaminobenzidine is subjected to the steps of washing, decolorization and crystallization to obtain a high-purity target product, where the purity of the target product can be as high as 94% or above.

Implementations of the present invention are described below by particular specific embodiments, and other advantages and effects of the present invention can be easily understood by persons skilled in the art based on the contents disclosed in this specification. The present invention may also be implemented or applied in other different specific implementations, and various modifications or changes of various details in this specification may also be conducted based on different viewpoints and applications without departing from the spirit of the present invention.

Example 1

First step: Preparation of 4,4'-biphenyl bis(N,N-dimethylaminosulfonate)

4,4'-biphenol (186.0 g/1.0 mol) and 900 ml of dioxane were put into a reactor in sequence, and stirring was conducted for uniform mixing. N,N-dimethylsulfamoyl chloride (330.0 g/2.3 mol) was slowly added to the reactor in a flowing sate under a normal temperature condition.

After the addition was completed, the temperature was slowly raised to 50-60° C. to carry out a reaction continuously for 2 h. Sampling was conducted for monitoring until the raw material content was less than 0.5% (HPLC-Area %), then cooling was conducted, and a reaction solution was directly used in a next reaction.

Second step: Preparation of 3,3'-dichloro-4,4'-biphenyl bis(N,N-dimethylaminosulfonate) Under a normal temperature condition, 380 ml of concentrated hydrochloric acid was added to the reaction solution obtained in the first step, and stirring was conducted for uniform mixing. An aqueous solution of sodium chlorate (37.2 g/0.35 mol, including 100 ml of water) was slowly added in a flowing state. After the addition was completed, the temperature was raised to 75-85° C. to carry out a reaction continuously for 6 h. Sampling was conducted for monitoring until the content of the 4,4'-biphenyl bis(N,N-dimethylaminosulfonate) was less than 1.0% (HPLC-Area %), and the reaction was stopped. Then, a resulting reaction solution was cooled to normal temperature and transferred to a washing kettle, and 150 ml of water was added and uniformly stirred. Filtration was conducted, and then a filter cake was washed with 200 ml of water for two times and 200 ml of methanol for one time, followed by filtration and drying to obtain 410.7 g of 3,3'-dichloro-4,4'-biphenyl bis(N,N-dimethylaminosulfonate) with a content of 95.2%.

The two-step yield of the first step and the second step was 83.3%.

Third step: Preparation of 3,3'-diaminobenzidine (DAB)

The 3,3'-dichloro-4,4'-biphenyl bis(N,N-dimethylaminosulfonate) (410.7 g/0.83 mol) and 25% ammonia water (800 g) were added in sequence to a beater cooled with ice water. After beating was conducted, a resulting mixture was transferred into an autoclave in which cuprous chloride (0.65 g), proline (8.1 g) and tetrabutylammonium chloride (8.2 g) were put in advance. Nitrogen replacement was conducted for four times, and 25% ammonia water (300 g) was used for washing the beater and then transferred into the autoclave, where the temperature of the system in the whole process was controlled not to exceed 10° C. Stirring was conducted, and ammonia gas (265 g) was continuously introduced into the autoclave. The autoclave was sealed and heated.

The system was heated to 170° C. for about 1.5 h to carry out a heat preservation reaction at a pressure of 2.7 MPa for 3 h. The system was then heated to 180° C. for about 0.5 h to carry out a heat preservation reaction at a pressure of 3.2 MPa for 3 h.

The heating was stopped, the autoclave was cooled to 130° C. at normal temperature, ammonia discharge and cooling were conducted at a pressure of 1.5-2.0 MPa, and when cooled to 70-80° C., the autoclave was back-flushed with nitrogen to realize discharge into a cooling kettle. The material solution was continuously cooled to 10-15° C., followed by pressure filtration. A filter cake was washed with 25% ammonia water (200 g) for three times and then washed with water (200 g) for three times to obtain about 190 g of a crude product, where the whole washing process was performed under the protection of nitrogen.

The crude product was put into a decolorization kettle, 3,500 g of methanol and 8.0 g of activated carbon were added, and heating reflux was conducted under the protection of nitrogen replacement for about 1 h. Then, pressure filtration was conducted with a sand core funnel at high temperature, and a filter cake was washed with 100 g of hot water. Filtrates were combined and cooled to 10-15° C. Then, suction filtration was conducted, and a resulting filter cake was subjected to vacuum drying at 70° C. for 5 h to obtain 167.7 g of a solid product with a content of 96.4% and a one-step yield of 91.0%.

The total reaction yield of the three steps was 75.8%.

Example 2

First step: Preparation of 4,4'-biphenyl bis(N,N-dimethylaminosulfonate)

4,4'-biphenol (186.0 g/1.0 mol) and 900 ml of sulfolane were put into a reactor in sequence, and stirring was conducted for uniform mixing. N,N-dimethylsulfamoyl chloride (430.5 g/3.0 mol) was slowly added to the reactor in a flowing sate under a normal temperature condition. After the addition was completed, the temperature was slowly raised to 50-60° C. to carry out a reaction continuously for 1.5 h. Sampling was conducted for monitoring until the raw material content was less than 0.5% (HPLC-Area %), then cooling was conducted, and a reaction solution was directly used in a next reaction.

Second step: Preparation of 3,3'-dichloro-4,4'-biphenyl bis(N,N-dimethylaminosulfonate)

Under a normal temperature condition, 700 ml of concentrated hydrochloric acid was added to the reaction solution obtained in the first step, and stirring was conducted for uniform mixing. An aqueous solution of sodium chlorate (53.2 g/0.50 mol, including 130 ml of water) was slowly added in a flowing state. After the addition was completed, the temperature was raised to 75-85° C. to carry out a reaction continuously for 5 h. Sampling was conducted for monitoring until the content of the 4,4'-biphenyl bis(N,N-dimethylaminosulfonate) was less than 1.0% (HPLC-Area %), and the reaction was stopped. Then, a resulting reaction solution was cooled to normal temperature and transferred to a washing kettle, and 180 ml of water was added and uniformly stirred. Filtration was conducted, and then a filter cake was washed with 200 ml of water for two times and 200 ml of methanol for one time, followed by filtration and drying to obtain 403.0 g of 3,3'-dichloro-4,4'-biphenyl bis(N,N-dimethylaminosulfonate) with a content of 94.1%.

The two-step yield of the first step and the second step was 80.8%.

Third step: Preparation of 3,3'-diaminobenzidine (DAB)

The 3,3'-dichloro-4,4'-biphenyl bis(N,N-dimethylaminosulfonate) (403.0 g/0.81 mol) and 25% ammonia water (800 g) were added in sequence to a beater cooled with ice water. After beating was conducted, a resulting mixture was transferred into an autoclave in which cuprous chloride (0.65 g), proline (5.1 g) and tetrabutylammonium chloride (8.2 g) were put in advance. Nitrogen replacement was conducted for four times, and 25% ammonia water (300 g) was used for washing the beater and then transferred into the autoclave, where the temperature of the system in the whole process was controlled not to exceed 10° C. Stirring was conducted, and ammonia gas (265 g) was continuously introduced into the autoclave. The autoclave was sealed and heated.

The system was heated to 170° C. for about 1.5 h to carry out a heat preservation reaction at a pressure of 2.7 MPa for 3 h. The system was then heated to 180° C. for about 0.5 h to carry out a heat preservation reaction at a pressure of 3.2 MPa for 3 h.

The heating was stopped, the autoclave was cooled to 130° C. at normal temperature, ammonia discharge and cooling were conducted at a pressure of 1.5-2.0 MPa, and when cooled to 70-80° C., the autoclave was back-flushed with nitrogen to realize discharge into a cooling kettle. The material solution was continuously cooled to 10-15° C., followed by pressure filtration. A filter cake was washed with 25% ammonia water (200 g) for three times and then washed with water (200 g) for three times to obtain about 183 g of a crude product, where the whole washing process was performed under the protection of nitrogen.

The crude product was put into a decolorization kettle, 3,500 g of methanol and 8.0 g of activated carbon were added, and heating reflux was conducted under the protection of nitrogen replacement for about 1 h. Then, pressure filtration was conducted with a sand core funnel at high temperature, and a filter cake was washed with 100 g of hot water. Filtrates were combined and cooled to 10-15° C. Then, suction filtration was conducted, and a resulting filter cake was subjected to vacuum drying at 70° C. for 5 h to obtain 164.4 g of a solid product with a content of 95.5% and a one-step yield of 90.8%.

The total reaction yield of the three steps was 73.4%.

Example 3

First step: Preparation of 4,4'-biphenyl bis(N,N-dimethylaminosulfonate)

4,4'-biphenol (186.0 g/1.0 mol) and 750 ml of dioxane were put into a reactor in sequence, and stirring was conducted for uniform mixing. N,N-dimethylsulfamoyl chloride (358.8 g/2.5 mol) was slowly added to the reactor in a flowing sate under a normal temperature condition. After the addition was completed, the temperature was slowly raised to 40-50° C. to carry out a reaction continuously for 3 h. Sampling was conducted for monitoring until the raw material content was less than 0.5% (HPLC-Area %), then cooling was conducted, and a reaction solution was directly used in a next reaction.

Second step: Preparation of 3,3'-dichloro-4,4'-biphenyl bis(N,N-dimethylaminosulfonate)

Under a normal temperature condition, 380 ml of concentrated hydrochloric acid was added to the reaction solution obtained in the first step, and stirring was conducted for uniform mixing. An aqueous solution of sodium chlorate (26.6 g/0.25 mol, including 80 ml of water) was slowly added in a flowing state. After the addition was completed, the temperature was raised to 80-90° C. to carry out a reaction continuously for 8 h. Sampling was conducted for monitoring until the content of the 4,4'-biphenyl bis(N,N-dimethylaminosulfonate) was less than 1.0% (HPLC-Area %), and the reaction was stopped. Then, a resulting reaction solution was cooled to normal temperature and transferred to a washing kettle, and 150 ml of water was added and uniformly stirred. Filtration was conducted, and then a filter cake was washed with 200 ml of water for two times and 200 ml of methanol for one time, followed by filtration and drying to obtain 387.8 g of 3,3'-dichloro-4,4'-biphenyl bis(N,N-dimethylaminosulfonate) with a content of 93.8%.

The two-step yield of the first step and the second step was 77.5%.

Third step: Preparation of 3,3'-diaminobenzidine (DAB)

The 3,3'-dichloro-4,4'-biphenyl bis(N,N-dimethylaminosulfonate) (387.8 g/0.78 mol) and 25% ammonia water (800 g) were added in sequence to a beater cooled with ice water. After beating was conducted, a resulting mixture was transferred into an autoclave in which cuprous chloride (0.65 g), a copper powder (8.1 g), proline (15.5 g) and tetrabutylammonium chloride (8.2 g) were put in advance. Nitrogen replacement was conducted for four times, and 25% ammonia water (300 g) was used for washing the beater and then transferred into the autoclave, where the temperature of the system in the whole process was controlled not to exceed 10° C. Stirring was conducted, and ammonia gas (265 g) was continuously introduced into the autoclave. The autoclave was sealed and heated.

The system was heated to 170° C. for about 1.5 h to carry out a heat preservation reaction at a pressure of 2.7 MPa for 3 h. The system was then heated to 180° C. for about 0.5 h to carry out a heat preservation reaction at a pressure of 3.2 MPa for 3 h.

The heating was stopped, the autoclave was cooled to 130° C. at normal temperature, ammonia discharge and cooling were conducted at a pressure of 1.5-2.0 MPa, and when cooled to 70-80° C., the autoclave was back-flushed with nitrogen to realize discharge into a cooling kettle. The material solution was continuously cooled to 10-15° C. under the protection of nitrogen, followed by pressure filtration. A filter cake was washed with 25% ammonia water (200 g) for three times and then washed with water (200 g) for three times to obtain about 186 g of a crude product, where the whole washing process was performed under the protection of nitrogen.

The crude product was put into a decolorization kettle, 3,500 g of methanol and 8.0 g of activated carbon were added, and heating reflux was conducted under the protection of nitrogen replacement for about 1 h. Then, pressure filtration was conducted with a sand core funnel at high temperature, and a filter cake was washed with 100 g of hot water. Filtrates were combined and cooled to 10-15° C. Then, suction filtration was conducted, and a resulting filter cake was subjected to vacuum drying at 70° C. for 5 h to obtain 160.1 g of a solid product with a content of 95.7% and a one-step yield of 91.8%.

The total reaction yield of the three steps was 71.10%.

The test data in the embodiments show that the total reaction yield (namely, conversion rate of dichlorobiphenyl-diamine) of the method for preparing 3,3'-diaminobenzidine provided in the embodiments of the present invention can reach more than 70%, and the product purity is greater than 94%, so that the method is more suitable for industrial-scale production.

Thus, persons skilled in the art should know that although a variety of exemplary embodiments of the present invention have been shown and described in detail herein, many other variations or modifications consistent with the principles of the present invention may still be directly identified or deduced from the disclosed contents of the present invention without departing from the spirit and scope of the present invention. Therefore, the scope of the present invention shall be understood and assumed as covering all such other variations or modifications.

What is claimed is:

1. A method for preparing 3,3'-diaminobenzidine, comprising:
    step S1: subjecting 4,4'-biphenol and N,N-dimethylsulfamoyl chloride to an esterification reaction in a first solvent at 40-70° C. to obtain 4,4'-biphenyl bis(N,N-dimethylaminosulfonate) as a first intermediate;
    step S2: subjecting the 4,4'-biphenyl bis(N,N-dimethylaminosulfonate) to a chlorination reaction with a chlorinating reagent under acidic conditions to obtain 3,3'-dichloro-4,4'-biphenyl bis(N,N-dimethylaminosulfonate) as a second intermediate;
    step S3: subjecting the second intermediate 3,3'-dichloro-4,4'-biphenyl bis(N,N-dimethylaminosulfonate) to an ammonolysis reaction with an ammoniation reagent in the presence of a combined catalyst to obtain a crude product of 3,3'-diaminobenzidine, wherein the combined catalyst is a mixture of proline, a cuprous salt and a phase transfer catalyst; and
    step S4: subjecting the crude product of 3,3'-diaminobenzidine to post-treatment to obtain a purified product of 3,3'-diaminobenzidine.

2. The method for preparing 3,3'-diaminobenzidine according to claim 1, wherein
    in the step S1, the molar amount of the N,N-dimethylsulfamoyl chloride is 2.2-3 times of that of the 4,4'-biphenol; and
    the first solvent is one of or a mixture of tetrahydrofuran, dioxane, N,N-dimethylformamide, sulfolane and toluene, and the volume amount of the first solvent is 4-10 times of the mass of the 4,4'-biphenol.

3. The method for preparing 3,3'-diaminobenzidine according to claim 1, wherein
    in the step S2, the chlorinating reagent includes concentrated hydrochloric acid and sodium chlorate;
    the volume amount of the concentrated hydrochloric acid is 1-4 times of the mass of the 4,4'-biphenol; and
    the molar amount of the sodium chlorate is 25-50% of that of the 4,4'-biphenol.

4. The method for preparing 3,3'-diaminobenzidine according to claim 3, wherein
    the volume amount of the concentrated hydrochloric acid is 2-3 times of the mass of the 4,4'-biphenol; and
    the molar amount of the sodium chlorate is 35-40% of that of the 4,4'-biphenol.

5. The method for preparing 3,3'-diaminobenzidine according to claim 1, wherein
    in the step S2, the chlorination reaction is carried out at a temperature of 50-90° C. for 5-10 h.

6. The method for preparing 3,3'-diaminobenzidine according to claim 5, wherein
    the chlorination reaction is carried out at a temperature of 75-85° C.

7. The method for preparing 3,3'-diaminobenzidine according to claim 1, wherein
    in the step S3, the ammoniation reagent comprises one or more of liquid ammonia, ammonia water and an ammonia-methanol solution; and
    the ammonolysis reaction is carried out at a temperature of 170-180° C. and a pressure of 2.5-3.5 Mpa for 5-10 h.

8. The method for preparing 3,3'-diaminobenzidine according to claim 1, wherein
    in the step S3, the mass amount of the proline is 1.0-5.0% of the mass of the 3,3'-dichloro-4,4'-biphenyl bis(N,N-dimethylaminosulfonate);
    the cuprous salt comprises one or more of cuprous chloride, cuprous sulfate and cuprous nitrate, and the mass amount of the cuprous salt is 0.1-0.5% of the mass of the 3,3'-dichloro-4,4'-biphenyl bis(N,N-dimethylaminosulfonate); and
    the phase transfer catalyst comprises one or more of tetrabutylammonium bromide, tetrabutylammonium chloride, triethylbenzylammonium bromide, triethylbenzylammonium chloride and an imidazoline quaternary ammonium salt, and the mass amount of the phase transfer catalyst is 1.0-5.0% of the mass of the 3,3'-dichloro-4,4'-biphenyl bis(N,N-dimethylaminosulfonate).

9. The method for preparing 3,3'-diaminobenzidine according to claim 1, wherein the step S4 specifically comprises:
    cooling the crude product of 3,3'-diaminobenzidine to 10-15° C. under a protective atmosphere;
    washing the crude product of 3,3'-diaminobenzidine;
    dissolving the washed crude product of 3,3'-diaminobenzidine in a second solvent, and adding a decolorizing agent for decolorization treatment;
    conducting filtration, and cooling a resulting filtrate to 10-15° C. for crystallization;
    and conducting filtration and drying to obtain the purified product of 3,3'-diaminobenzidine.

10. The method for preparing 3,3'-diaminobenzidine according to claim 1, wherein the step S1 and the step S2 are performed in a same reactor.

* * * * *